United States Patent [19]

Keen

[11] Patent Number: 4,578,524

[45] Date of Patent: Mar. 25, 1986

[54] CARBON DIOXIDE-ENHANCED MONOALKYLENE GLYCOL PRODUCTION

[75] Inventor: Brian T. Keen, Charleston, W. Va.

[73] Assignee: Union Carbide Corporation, Danbury, Conn.

[21] Appl. No.: 594,265

[22] Filed: Mar. 28, 1984

[51] Int. Cl.$^4$ ............... C07C 31/20; C07C 33/26; C07C 35/14; C07C 33/035

[52] U.S. Cl. .......................... 568/867; 568/811; 568/833; 568/857

[58] Field of Search ............... 568/867, 833, 811, 857

[56] References Cited

U.S. PATENT DOCUMENTS 4,277,632  7/1981  Kumazawa et al. ............... 568/867

FOREIGN PATENT DOCUMENTS 5673036  11/1979  Japan.
73035   6/1981   Japan ............... 568/867
56-92228  7/1981  Japan.

OTHER PUBLICATIONS

USPA Ser. No. 530,235 (Atty Docket 13486-1) filed 9/8/83.

Primary Examiner—J. E. Evans
Attorney, Agent, or Firm—Steven T. Trinker

[57] ABSTRACT

The process for the liquid-phase hydration of a vicinal alkylene oxide(s) to the corresponding alkylene glycol(s) comprising carrying out such hydration in the presence of vanadate anion and a selectivity-enhancing amount of carbon dioxide.

15 Claims, No Drawings

CARBON DIOXIDE-ENHANCED MONOALKYLENE GLYCOL PRODUCTION

This invention relates to processes for the hydrolysis of vicinal alkylene oxides to the corresponding alkylene glycols in the presence of vanadate anion in a liquid menstruum and in the presence of a selectivity-enhancing amount of carbon dioxide.

BACKGROUND OF THE INVENTION

Alkylene oxides, for example, ethylene oxide, propylene oxide and butylene oxide, have been subjected to liquid-phase hydration to produce the corresponding alkylene glycols. Commercially, in the production of ethylene glycol from ethylene oxide large molar excesses of water are used (See, Kirk-Othmer, Encyclopedia of Chemical Technology Volume 11, Third Edition, Page 939, (1980)). It has been reported that the presence of large quantities of water in the reaction system are necessary if the yield to the desired monoalkylene glycol is to be great enough to be commercially viable and minimize the production of by-products such as diglycols and triglycols. Accordingly, the commercial practice has generally involved the hydration of an alkylene oxide at a temperature of about 100° C. to about 200° C. in the presence of a large molar excess of water, for example, in excess of 15 moles of water per mole of alkylene oxide, when the corresponding monoalkylene glycol is to be produced. Unfortunately, the use of such large excesses of water presents significant energy and equipment requirements for its removal.

since the selectivity of the hydration process to monoglycol, e.g., ethylene glycol, propylene glycol or butylene glycol, is dependent on the by-products formed, it would be desirable to provide a process that would increase the selectivity of the hydration process to monoglycol products. In addition, any process which would favorably decrease the relative amount of water employed to alkylene oxide hydrated while not increasing, or preferably decreasing, the by-products formed would be advantageous. Thus, the energy and equipment requirements would necessarily be less for separation and purification processes relating to the removal and recovery of the monoglycol from water and by-products.

Several processes have been suggested for the hydration of an alkylene oxide in the presence of a specific catalyst such that the ratio of water to alkylene oxide may be lowered and such that the selectivity to monoglycol product may be maintained or enhanced.

Numerous catalysts have been suggested for use in the hydration of alkylene oxides, including the use of acid catalysts such as: alkyl sulfonic acid ion exchange resins (U.S. Pat. No. 4,165,440); carboxylic acids and halogen acids (U.S. Pat. No. 4,112,054); strong acid cation exchange resins (U.S. Pat. No. 4,107,221); aliphatic monocarboxylic and/or polycarboxylic acids (U.S. Pat. No. 3,933,923); cationic exchange resins (U.S. Pat. No. 3,062,889); acidic zeolites (U.S. Pat. No. 3,028,434); sulfur dioxide (U.S. Pat. No. 2,807,651); $Ca_3(PO_4)_2$ (U.S. Pat. No. 2,770,656); high-melting polyvalent metal fluorides (U.S. Pat. No. 2,547,766); trihalogen acetic acid (U.S. Pat. No. 2,472,417); and copper-promoted aluminum phosphate (U.S. Pat. No. 4,014,945).

In addition to the acid catalysts, numerous catalysts have been suggested for the hydration of alkylene oxides in the presence of carbon dioxide. These include alkali metal halides, such as chlorides, bromides and iodides, quaternary ammonium halides such as tetramethyl ammonium iodide and tetramethyl ammonium bromide (British Patent No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); and chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Although a review of the results reported in the patent literature would suggest that the above-described catalysts have provided commercially acceptable results, that is, a high selectivity to the monoglycol product and a decrease in the requirement for large molar excess of water, these catalysts have not been commercially employed for several reasons. For example, alkali metal halides tend to corrode the reaction system at the temperatures employed for the hydration of alkylene oxides. The relatively low solubility of alkali metal halides and quaternary ammonium halides in alkylene glycol restricts their use as hydration catalysts since they are likely to precipitate within the reaction system during the course of the hydration reaction and can result in problems associated with cleaning the reaction system. In addition, some catalysts, such as tertiary amines, have certain chemical and physical properties which prevent their ready use as hydration catalysts. For example, tertiary amines have a strong pungent odor which is not desirable in manufacturing and can detract from the quality of the end product.

U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming the appreciable amounts of by-products, such as the polyglycols. The reaction may be carried out in the presence of carbon dioxide. The patentees state that the process can be effectively carried out in the presence of from 0.00001 to 1, preferably from 0.0001 to 1, mole of carbon dioxide per mole of alkylene oxide. In the examples, where carbon dioxide was employed (either as carbon dioxide or a bicarbonate salt), the amount ranged from 0.001 to 0.08 mole of carbon dioxide per mole of ethylene oxide. When the reaction is carried out in the presence of nitrogen, air, etc. the patentees state that the pH of the reaction mixture should be adjusted to a value in the range of 5 to 10. Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The amount of carbon dioxide to be employed in the disclosed process is within the range of 0.00001 to 1, preferably, 0.0001 to 1, mole of carbon dioxide per mole of alkylene oxide. The compounds employed as the catalysts include the oxides, sulfides, acids, halides, phosphorous compounds, polyacids, alkali metal salts of acids and polyacids, ammonium salts of acids and polyacids, and heavy metal salts of acids. Although the examples show the use of various metal catalysts, the disclosure does not disclose any detail as to the nature of the hydration process and the selection of the catalysts employed therein. In example 2, the process is carried out using a potassium vanadate as the hydration catalyst for the production of ethylene glycol from ethylene oxide and water under a carbon dioxide pressure. No identification of the vanadate used was made. The carbon dioxide was provided in the amount of 0.01 mole per mole of ethylene oxide. The conversion of ethylene oxide to products is reported to be 100 percent but the selectivity to monoethylene glycol is only 50 percent. The combined selectivity to diethylene glycol and triethylene glycol is also 50 percent. Thus, example 2 shows that the use of potassium vanadate was only slightly better than the obtained 36.1 percent selectivity reported for the conversion of ethylene oxide to ethylene glycol wherein no catalyst was employed (see comparative example 1 of JA 56/073,035).

Japanese Kokai No. JA 56/92228, published July 25, 1981, is directed to processes for producing highly pure alkylene glycols. The disclosure is directed to a distillation procedure for recovery of a molybdenum and/or tungsten-containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

J. H. Robson and G. E. Keller, II, in copending U.S. patent application Ser. No. 530,235, filed Sept. 8, 1983, herein incorporated by reference, disclose the use of water-soluble vanadate salts at a pH of between 5 and 12 to enhance the selectivity of the hydration of alkylene oxides to monoalkylene glycols. One preferred vanadate salt comprises metavanadate, and it is reported that carbon dioxide decreases the selectivity to the monoalkylene glycol product when using this salt. Thus, when substantially all of the vanadate anion is believed to be metavanadate anion, carbon dioxide is disclosed to be desirably less than about 0.10, preferably less than 0.05, mole per mole of alkylene oxide.

OVERVIEW OF THE INVENTION

This invention relates to processes for the production of the corresponding monoalkylene glycol by the hydration in a liquid phase of alkylene oxide in the presence of vanadate anion and in the presence of a selectivity-enhancing amount of carbon dioxide. The amount of carbon dioxide that provides the enhancing effect falls within a narrow range as set forth below and is believed to be dependent upon the vanadate species present.

The processes of this invention provide enhanced selectivity to monoalkylene glycol. Thus, the selectivities achievable using this invention are greater than those obtained under common conditions including using vanadate anion but not using the amounts of carbon dioxide in accordance with the invention.

DETAILED DESCRIPTION OF THE INVENTION

This invention relates to processes for the production of monoalkylene glycols by the reaction of water with vicinal alkylene oxide having the general formula

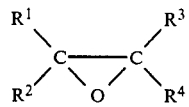

wherein $R^1$, $R^2$, $R^3$ and $R^4$ each designate a hydrogen atom, an alkyl group having between 1 and about 10 carbon atoms, an aryl group having at least 6 carbon atoms (e.g., monocyclic or bicyclic aryl), an alkenyl group having 2 or 3 carbon atoms or a cycloalkyl group having 3 to 6 carbon atoms. Representative of the alkylene oxides which may be employed in the instant invention are ethylene oxide, propylene oxide, butylene oxide (including isobutylene oxide, 1,2-butylene oxide and 2,3-butylene oxide), pentylene oxide, cyclohexene oxide, styrene oxide, and the like. Preferably, the alkylene oxide is an aliphatic alkylene oxide such as ethylene oxide and propylene oxide.

The source of the alkylene oxide is not generally important, and alkylene oxide formed by most any process may be employed in the instant invention. For example, if ethylene oxide is the selected alkylene oxide it may be formed by the catalytic oxidation of ethylene with molecular oxygen or an oxygen-containing gas in the presence of a silver catalyst. Such a process for forming the ethylene oxide employed herein is particularly desirable since substantially pure ethylene oxide may be obtained.

The process also employs water as a reagent for the formation of the corresponding alkylene glycol. The source of the water is not important. Demineralized water obtained by, for example, ion exchange treatment, or other water of sufficient purity is usable in hydration processes. The amount of water to be used, relative to a mole of alkylene oxide, is generally between about 1 and about 40 moles, preferably up to about 30 moles, say, between about 1 and 30 moles and preferably between about 1 and 20 moles, and about 1 to about 10 moles if reducing energy and equipment costs for glycol-water separation is a primary objective. Although the molar ratio of water required for hydrolysis to alkylene oxide may be decreased below about 5 moles of water per mole of alkylene oxide, it is generally desirable to maintain at least a slight molar excess of water over the stoichiometric amount of water to ensure a higher selectivity of alkylene oxide to the monoalkylene glycol product. Thus, by the use of vanadate anion and carbon dioxide in accordance with this invention and the molar ratio of water to alkylene oxide (i.e., molar hydrolysis ratio), commercially-attractive selectivities to monoalkylene glycol can be obtained, e.g., greater than about 70, say, greater than about 80, percent (mole basis).

The processes of this invention employ a vanadate-containing adjuvant comprising one or more vanadate salts represented by the formula:

$$(R)_p^{+a}(A)^{-q}$$

wherein p times a equals q; R is a dissociatable cation in water; and A is a vanadate anion. Vanadate chemistry is complex and numerous vanadate anions species, e.g., metavanadate, hydrogen pyrovanadate, pyrovanadate and orthovanadate anions, have been identified although their specific structures are not fully known. For purposes of discussion, common structural reference to these anions is as follows: metavanadate, $(VO_3)^-$; hydrogen pyrovanadate $(HV_2O_7)^{3-}$; pyrovanadate, $(V_2O_7)^{4-}$; and orthovanadate, $(VO_4)^{3-}$. The particular vanadate species present is thought to be dependent on the pH of the liquid phase. Hence, at a pH of, say, about 12, little, if any, metavanadate anion may exist. Although the processes are carried out by providing a water-soluble vanadate salt to the reaction system, the exact nature of the catalytic species is not fully known.

For purposes of describing the invention, it will be assumed that the vanadate anion can be characterized in terms of a mixture of metavanadate and orthovanadate, that is, a calculated mole ratio of these two anions. For example, pyrovanadate can be expressed as a mixture of one mole of metavanadate and one mole of orthovanadate; i.e., $VO_3^- + VO_4^{3-}$ equals $V_2O_7^{4-}$, and hydrogen pyrovanadate can be expressed as the mole ratio of metavanadate to orthovanadate of 3:1. The calculated mole ratio of metavanadate to orthovanadate for the vanadate anion useful in accordance with this invention is less than 2.2:1, and is often in the range of about 0.001:1 to 2.0:1, preferably about 0.1:1 to 1.5:1.

The calculated mole ratio of metavanadate to orthovanadate is determined prior to the addition of carbon dioxide. The calculated mole ratio may be determined from an analysis of the vanadate species in the reaction medium, e.g., by nuclear magnetic resonance spectroscopy, and then calculating the amounts of metavanadate and orthovanadate required to provide the concentrations of the observed vanadates. Alternatively, the ratio may be determined directly from using metavanadate and orthovanadate as the adjuvants. If the latter method is employed, it should be recognized that the addition of an acid or base could change the mole ratio of metavanadate to orthovanadate.

The cation to the vanadate anion will permit the vanadate anion to become dissociated in water. While cations which provide water soluble vanadate-containing compounds, under reaction conditions, such as the alkali metal salts, quaternary ammonium salts, ammonium salts, and the like, are useful, cations which are substantially insoluble, or have little solubility, in water at reaction conditions can be used providing that the vanadate anion is able to interact with the alkylene oxide. This activity is believed to exist when the vanadate anion is capable of being dissociated from the cation. Thus, calcium vanadate, which has little solubility in water and retains the vanadate anion tightly bound, has not been found to be an acceptable vanadate-containing compound. On the other hand, where the cation is an essentially insoluble quaternary ammonium moiety, the dissociatable nature of the vanadate anion is believed to permit its usefulness in accordance with the invention.

Thus, suitable cations may include structures represented by the formulae:

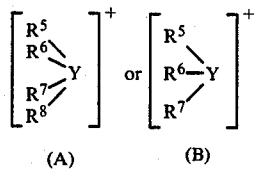

where Y is nitrogen, phosphorous, or arsenic (formula A), or sulfur (formula B), i.e., ammoniums, phosphoniums, arsoniums and sulfoniums, where each of $R^5$, $R^6$, $R^7$ and $R^8$ may be the same or different and may combine to form cyclic structures. Exemplary of each of $R^5$, $R^6$, $R^7$ and $R^8$ are hydrogen and unsubstituted and substituted hydrocarbyls of 1 or more carbon atoms, e.g., to about 70 carbon atoms. Representative cations are disclosed in copending U.S. patent application Ser. No. 594,264, filed on even date herewith, of J. R. Briggs and J. H. Robson, herein incorporated by reference. At least one of $R^5$, $R^6$, $R^7$ and $R^8$ may be bonded or complexed to an organic or inorganic solid. For example, in copending U.S. patent application Ser. No. 594,268, filed on even date herewith, of R. D. Best, J. A. Collier, B. T. Keen, and J. H. Robson, herein incorporated by reference, anion exchange resins are disclosed which have electropositive complexing sites which, among other possibilities, can be quaternary ammonium or quaternary phosphonium moieties that are in association with the vanadate anion. Other organic-containing cations which may be useful include the bis(hydrocarbyl-phosphine)iminiums represented by the formula $$[(R_3^9P)_2N]^+$$

wherein each $R^9$ may be the same or different and maybe the same as set forth for $R^5$ to $R^8$. Illustrative iminiums are disclosed in Ser. No. 594,264.

The vanadate anion may be provided to the reaction mixture as a vanadate anion or in a form which is converted to the desired vanadate anion by subsequent chemical reaction. Hence, halide, sulfide, or the like, vanadium-containing compounds may be employed as the precursor to the desired vanadate anion. Some of these precursor compounds may be converted to vanadates during the hydration reaction.

The vanadate may be used in the salt form or may be introduced into the reaction system on a support, such as on a carrier such as silica, alumina, zeolites, clay, and the like. When the process is carried out, the vanadate is generally in a dissolved, mixed, suspended, or deposited form in a fixed bed in the liquid phase with the reactants, i.e., the alkylene oxide and water. The vanadate may be provided to the reaction system by mixing it with water being introduced into the reaction system, it may be introduced by means of a separate inlet to the reaction system, or it may be retained in the reaction zone as an immiscible organic phase or solid phase. When the vanadate-containing adjuvant is water-soluble, replenishing the reaction zone is desired. The exact means of introduction of the vanadate is not critical, and frequently the vanadate is provided at the beginning of the reaction and/or is continuously or intermittently added at a fixed rate during the reaction.

U.S. patent applications Ser. Nos. 594,256, filed on even date herewith, of J. R. Briggs and J. H. Robson, and 594,385, filed on even date herewith, of J. R. Briggs, G. L. O'Connor, and J. H. Robson, both of which are herein incorporated by reference, describe processes for making alkylene glycols from alkylene oxides in the presence of, inter alia, selectivity-enhancing vanadate anion using a two liquid phase reaction menstruum and a two step process wherein alkylene oxide is first contacted with the vanadate anion to form an associated moiety and then the associated moiety is contacted with water to form alkylene glycol.

The vanadate salt (calculated as metavanadate anion regardless of the form of the vanadate anion added to, or present in, the reaction system) is generally provided in an amount sufficient to enhance selectivity, e.g., at least 0.005 percent, based on the weight of the vicinal alkylene oxide employed, and is preferably employed in an amount between about 0.01 and about 90 percent by weight, and most preferably between about 0.05 and about 30 percent by weight, based on the weight of the alkylene oxide employed.

In accordance with this invention, the selectivity enhancement provided by carbon dioxide is achieved when employing certain ratios of carbon dioxide to vanadate anion. The amount of carbon dioxide provided per mole of vanadium atoms present is typically from about (a) 0.5-M/O to (b) 2.2-M/O, wherein M/O is the calculated mole ratio of metavanadate to orthovanadate with the proviso that at least 0.01 mole of carbon dioxide is provided per mole of vanadium atoms. Preferably, the mole ratio of carbon dioxide to vanadium atoms is in the range of about (a) 0.5-M/O to (b) 1.9-M/O, say, about (a) 0.7-M/O to (b) 1.8-M/O. In some instances, the mole ratio of carbon dioxide atoms to vanadium atoms is in the range of about (a) 0.75-M/O to (b) 1.5-M/O. In the event that carbon dioxide-consuming species are present in the reaction menstruum, the amount of carbon dioxide provided in accordance with this invention should be adjusted accordingly.

The carbon dioxide may be provided to the reaction zone in any convenient manner. The carbon dioxide may, for instance, be introduced separately and/or with one or more of the feed streams. When the alkylene oxide is produced by the partial oxidation of an alkane, carbon dioxide is generated. Hence, by the very nature of the process, some carbon dioxide is provided to the reaction system. In the event that the carbon dioxide present in the alkylene oxide feed stream is greater than that desired in the reaction zone, it may be flashed from the alkylene oxide or removed in another suitable manner. Advantageously, the carbon dioxide is relatively uniformly dispersed in the reaction medium.

At least a portion of the carbon dioxide may be added in other than that molecular form. For example, water soluble bicarbonate, e.g., as the alkali metal, alkaline earth metal, ammonium, etc., salts, or carbonic acid may provide a portion of the carbon dioxide. It should be noted that these species can affect the form of the vanadate. Hence, when employing a bicarbonate salt, the calculated mole ratio of metavanadate to orthovanadate may be increased. By the way of example, a mixture of two moles of metavanadate and two moles of bicarbonate may provide the same performance as obtained using a vanadate having a calculated mole ratio of metavanadate to orthovanadate of 1:1 and one mole of carbon dioxide per mole of vanadium atoms.

The production of alkylene glycol according to this invention is effectively carried out in the presence of a gas, such as air, argon, nitrogen, and the like, as a diluent for the reaction system.

The pH of the reaction system can affect the rate and, importantly, selectivity to monoalkylene glycol. Although the exact relationship of selectivity and pH is not yet known, it is believed that, for instance, a metavanadate anion may undergo in situ modification to provide the active species of vanadium or vanadate which provides the advantageous selectivities to monoethylene glycol. In general, the initial pH of the reaction system is between about 5 and about 12, e.g., about 7 to 11, and preferably, the pH is within the ranges during the process. It is believed that the pH should be between about 8.5 and about 10.5, say, about 9.2 to 10.5, and sometimes between about 9.6 and 10.3.

The pH may be affected by a number of mechanisms including the presence of carbon dioxide. For instance, acid or base such as sulfuric acid, hydrochloric acid, phosphoric acid, carbonic acid, alkali metal hydroxide (e.g., sodium hydroxide and potassium hydroxide), ammonium hydroxide and the like may be added. Preferably, an adjuvant, which is used to modify the pH, does not result in precipitation of the vanadate or does not otherwise untowardly affect the reaction system or products. In many instances, the pH is affected by the vanadate anion added and its concentration. For example, orthovanadate is strongly basic and may be used in combination with metavanadate or pyrovanadate as a means to adjust the pH. Similarly, the concentration of vanadate anion will affect the pH. It is believed, however, that carbon dioxide provides a greater enhancement of selectivity than that provided by an initial pH adjustment.

The process is usually carried out at a temperature between about 20° C. and about 250° C., preferably between about 50° C. and about 200° C. Temperatures above 250° C. may be employed depending on the selection of the alkylene oxide, vanadate salt compound and pressure employed; however, such high temperatures are not generally preferred.

The process is typically carried out at a pressure in the range between about 0 kg/cm$^2$G and about 1000 kg/cm$^2$G and preferably between about 2 kg/cm$^2$G and about 100 kg/cm$^2$G, although pressures outside these preferred ranges are believed to be operable.

The process of this invention can be operated in the presence of a water-miscible solvent which may serve to dilute the reaction mixtue. Any liquid which at the reaction temperature is totally miscible with the alkylene oxide water and the glycol product(s) can be a solvent, provided that it is not reactive with either the alkylene oxide reactant, the alkylene glycol produced or the vanadate salt employed. Thus, compounds such as carboxylic acid, phenols, aldehydes and alkylene carbonates are preferably not employed as solvents in the practice of this invention. The alkylene glycol product is often a very good solvent. If an alkylene glycol is employed as a solvent, preferably it is the same as the alkylene glycol product. The solvents are useful for the purpose of controlling reaction temperature (particularly at low hydrolysis ratios) and rate and are useful in recycle systems in continuous processes.

The processes of this invention may be carried out as a batch reaction or as a continuous process. Conventional autoclaves can be employed when using elevated temperatures, but glassware-type equipment can be used when operated at moderate pressures. Plug-flow reactors are often utilized in conventional continuous procedures. Solvent may be recycled and catalyst may be recovered.

The reaction may be carried out for very short periods of time, e.g., fractions of a second, and, if desired, may be carried out over reaction periods of up to hours. The process conditions are governed by the amounts of solvent and catalyst employed, the pressures and temperatures employed, and like considerations.

It has been observed that when the alkylene oxide is ethylene oxide, the selectivity to monoethylene glycol over diethylene glycol and triethylene glycol is greater than 70 molar percent and generally greater than 80 molar percent.

As can be seen from this disclosure, the combinations of hydrolysis ratio, vanadate concentration, carbon dioxide concentration and pH can be correlated to provide optional results for a particular objective. For example, if the objective is to provide high selectivity to monoalkylene glycol, higher hydrolysis ratios may be employed, and selectivities of greater than 95 percent at 20:1 molar hydrolysis ratios may be achievable. If the objective is to use low hyrolysis ratios to reduce the costs associated with the glycol-water separation, the comparable selectivities to those obtained in conventional hydrolysis operations may be achievable at low hydrolysis ratios. For example, selectivities of greater than 90 percent can be obtained at molar hydrolysis ratios of around 5:1.

The following examples show various modes in the practice of this invention but are not intended to limit the invention. All parts and percentages of solids are by weight and of liquids and gases are by volume unless otherwise indicated.

In the examples, the following analytical method was used. The samples are prepared by adding about 2 weight percent 1,3-butanediol as an internal standard. Approximately 50 microliters of this admixture are added to 1.0 milliliter of Regisil (TM) (BSTFA) (N,N-bistrimethylsilyl trifluoroacetamide), available from the Regis Chemical Company, Morton Grove, Ill., in a serum vial and mixed for at least about 12 hours. The weight percent monoethylene glycol, diethylene glycol and triethylene glycol are determined by standard vapor phase chromatography using a Hewlett Packard 5880 (TM) gas chromatograph equipped with a four meter by $\frac{1}{8}$ inch (0.32 centimeters) (outside diameter) stainless steel column packed with 20 percent OV-101 methylsilicone stationary liquid phase supported on 80/100 mesh Chromosorb W HP (TM) both available from Supelco, Inc. Bellefonte, Pa. The selectivity to each glycol component is calculated as the quotient of the weight percent of the subject glycol divided by the sum of the weight percents of each of the monoethylene glycol, diethylene glycol and triethylene glycol.

EXPERIMENTS 1 TO 4

These experiments were carried out with a stainless steel autoclave having an internal volume of about 300 cubic centimeters. Prior to the introduction of reactants to the autoclave, the autoclave was purged with nitrogen at ambient temperature (between about 18° C. and 22° C.). Water and sodium pyrovanadate (when employed) were charged into the autoclave, and then ethylene oxide was pressured into the autocalve which was maintained at about 60 pounds per square inch gauge pressure with nitrogen. Carbon dioxide (when employed) was then introduced into the autoclave. The autoclave was stirred and was heated with stirring and maintained at that temperature. During this time, the autoclave pressure rose, fell and stabilized. The autoclave and its contents were then cooled to ambient internal temperature, and the contents were analyzed. The details are provided in Table I.

TABLE I

| Experiment | Water, grams | Ethylene Oxide grams | $Na_4V_2O_7$ grams (mmol) | Mole Ratio $VO_3^-/VO_4^{3-}$ | $CO_2$, psig (mmol) | Ratio $CO_2/V$ | Reaction Temperature, °C. | Reaction Time, hr. | Selectivity To Monoethylene Glycol, wt. % |
|---|---|---|---|---|---|---|---|---|---|
| 1 Comparative | 67.1 | 32.7 | 1.6(5.5) | 1 | 10(6) | 0.55 | 127 | 1.7 | 89 |
| 2 | 67.0 | 32.5 | 1.6(5.5) | 1 | 0(0) | 0 | 137 | 1.7 | 83 |
| 3 | 67.1 | 32.9 | 1.6(5.5) | 1 | 30(10) | 1.65 | 130 | 1.5 | 81 |
| 4 | 67.0 | 33.0 | 0(0.) | — | 0(0) | 0 | 135 | 1.5 | 71 |

EXPERIMENTS 4 TO 15

Ethylene oxide and water stock solution were prepared in chilled (about 5° C.) 120 cubic centimeter serum bottles as follows:

Solution A: 75.0 g $H_2O$ and 25.0 g ethylene oxide.
Solution B: 70.0 g $H_2O$ and 10.0 g ethylene oxide.
Solution C: 75.0 g $H_2O$ (saturated with $CO_2$) and 25.0 g ethylene oxide.
Solution D: 70.0 g $H_2O$ (saturated with $CO_2$) and 10.0 g ethylene oxide.
Solution E: 75.0 g $H_2O$ (pH 4 by $H_2SO_4$ as a 1% aqueous solution) and 25.0 g ethylene oxide.
Solution F: 70.0 g $H_2O$ (pH 4 by $H_2SO_4$ as a 1% aqueous solution) and 10.0 g ethylene oxide.

Solutions C and D had an approximate pH of 4.

Sodium metavanadate and sodium orthovanadate were then introduced into chilled (about 5° C.) stainless seel microreactors, having a length of about 3.5 inches (8.9 centimeters) and outside diameter of 0.5 inches (1.3 centimeters). Because of the small amounts added, a source of imprecision existed. Six grams of the stock solution were then added. The microreactors were sealed and introduced into a constant temperature bath (135° C.) under constant mixing by a reciprocating motion. The reaction was conducted for two hours, the reactor contents cooled and analyzed. The experiments are summarized in Table II.

TABLE II

| Experiment | Stock Solution | NaVO$_3$, Milligrams | Na$_3$VO$_4$ Milligrams | Mole Ratio VO$_3^-$/VO$_4^{3-}$ | Ratio CO$_2$/V | Selectivity to Monoethylene Glycol, wt. % |
|---|---|---|---|---|---|---|
| 4 | A | 49 | 74 | 1 | 0 | 76.7 |
| 5 | B | 25 | 37 | 1 | 0 | 87.8 |
| 6 | A | 81 | 41 | 3 | 0 | 88.0 |
| 7 | B | 40 | 20 | 3 | 0 | 94.6 |
| 8 | C | 49 | 74 | 1 | 0.18 | 82.2 |
| 9 | D | 25 | 37 | 1 | 0.44 | 91.6 |
| 10 | C | 81 | 41 | 3 | 0.18 | 84.6 |
| 11 | D | 41 | 21 | 3 | 0.44 | 93.2 |
| 12 | C | — | 135 | 0 | 0.19 | 64.7 |
| 13 | D | — | 66 | 0 | 0.47 | 81.7 |
| 14 | E | 49 | 74 | 1 | 0 | 69.8 |
| 15 | F | 25 | 37 | 1 | 0 | 85.6 |

It is claimed:

1. A process for the production of monoalkylene glycol comprising reacting a vicinal alkylene oxide with water in the presence of (a) a vanadate-containing adjuvant to enhance the selectivity of the reaction to monoethylene glycol, said vanadate-containing adjuvant comprising at least one dissociatable metavanadate, hydrogen pyrovanadate, pyrovanadate and orthovanadate anion such that when the vanadate anions present are characterized as a mole ratio of metavanadate to orthovanadate, the mole ratio is less than 2.2:1, and (b) carbon dioxide in the amount of between about (i) 0.5-M/O to (ii) 2.2-M/O moles of carbon dioxide per mole of vanadium atoms, wherein M/O is the calculated mole ratio of metavanadate to orthovanadate characterizing the vanadate anions, provided that at least 0.01 mole of carbon dioxide is provided per mole of vanadium atoms.

2. The process of claim 1 wherein the mole ratio of carbon dioxide to vanadium atoms is between about (i) 0.7-M/O to (ii) 1.8-M/O.

3. The process of claim 2 wherein the calculated mole ratio of metavanadate to orthovanadate is between about 0.1:1 and 1.5:1.

4. The process of claim 3 wherein the vanadate adjuvant is a water-soluble vanadate compound.

5. The process of claim 3 wherein the pH during the reaction is between about 9.2 and 10.5.

6. The process of claim 3 wherein the reaction temperature is about 20° C. to 250° C. and the reaction pressure is between about 0 and about 1000 kg/cm$^2$G.

7. A process for the production of monoalkylene glycol comprising reacting in a liquid phase, a vicinal alkylene oxide of the formula:

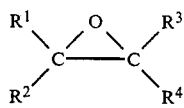

wherein R$^1$, R$^2$, R$^3$, and R$^4$ each designate a hydrogen atom, an alkyl group having between 1 and about 10 carbon atoms, an aryl group having at least 6 carbon atoms, an alkenyl group having 2 or 3 carbon atoms or a cycloalkyl group having 3 to 6 carbon atoms, with water in the presence of a sufficient amount of a vanadate-containing adjuvant to enhance the selectivity of the reaction to monoalkylene glycol, said vanadate-containing adjuvant comprising one or more vanadate compounds represented by the formula:

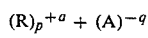

wherein p times a equals q; R is a cation which is dissociatable in water and A is metavanadate, hydrogen pyrovanadate, pyrovanadate, or orthovanadate, wherein, when the vanadate compounds are characterized as a mole ratio of metavanadate to orthovanadate, the mole ratio of metavanadate to orthovanadate is less than 2.2:1. wherein said process is conducted in the presence of a selectivity-enhancing amount of carbon dioxide per mole of vanadium atoms within the range of about (a) 0.5-M/O to (b) 2.2-M/O, wherein M/O is the mole ratio of metavanadate to orthovanadate characterizing the vanadate anions, provided that at least 0.01 mole of carbon dioxide is provided per mole of vanadium atoms.

8. The process of claim 7 wherein the molar ratio of water to alkylene oxide is less than about 30.

9. The process of claim 8 wherein the temperature of the reaction is between about 20° C. and 250° C.

10. The process of claim 8 wherein the pressure of the reaction is between about 0 kg/cm$^2$G and about 1000 kg/cm$^2$G.

11. The process of claim 8 wherein the pH is between about 8.5 and 10.5.

12. The process of claim 8 wherein the alkylene oxide is ethylene oxide.

13. The process of claim 8 wherein R is an alkali metal, ammonium or phosphonium cation.

14. The process of claim 13 wherein the calculated mole ratio of metavanadate to orthovanadate is between about 0.1:1 and 1.5:1.

15. The process of claim 14 wherein the mole ratio of carbon dioxide to vanadium atoms is between about (i) 0.7-M/O to (ii) 1.8-M/O and the pH is between about 9.2 and 10.5.

* * * * *